(12) United States Patent
Lin et al.

(10) Patent No.: US 9,260,364 B2
(45) Date of Patent: *Feb. 16, 2016

(54) CATALYTIC OR PHOTOCATALYTIC PREPARATION METHOD OF PARYLENE AF4

(71) Applicant: Yuan-Shin Materials Technology Corp., Taipei (TW)

(72) Inventors: Chun-Hsu Lin, Taipei (TW); Chien-Yi Sun, Kaohsiung (TW); Yung-Yu Yin, Pingtung County (TW); Chun-Shih Li, Pingtung County (TW); Yo-Chun Chou, Taichung (TW)

(73) Assignee: YUAN-SHIN MATERIALS TECHNOLOGY CORP., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/687,257

(22) Filed: Apr. 15, 2015

(65) Prior Publication Data

US 2015/0218067 A1    Aug. 6, 2015

Related U.S. Application Data

(62) Division of application No. 13/623,926, filed on Sep. 21, 2012, now Pat. No. 9,056,809.

(30) Foreign Application Priority Data

Jul. 16, 2012 (TW) .............................. 101125578 A

(51) Int. Cl.
  *C07C 17/269* (2006.01)
  *C07C 23/18* (2006.01)

(52) U.S. Cl.
  CPC ............... *C07C 17/269* (2013.01); *C07C 23/18* (2013.01); *C07C 2103/92* (2013.01)

(58) Field of Classification Search
  CPC .............................. C07C 17/269; C07C 23/18
  See application file for complete search history.

(56) References Cited

U.S. PATENT DOCUMENTS

| | | |
|---|---|---|
| 5,536,892 A | 7/1996 | Dolbier et al. |
| 5,841,005 A | 11/1998 | Dolbier et al. |

FOREIGN PATENT DOCUMENTS

| | | |
|---|---|---|
| CN | 1295996 A | 5/2001 |
| EP | 0971867 B1 | 1/2004 |
| JP | H11513689 A | 11/1999 |
| JP | 2001515507 A | 9/2001 |

OTHER PUBLICATIONS

Shi-Zheng Zhu, Yun-Yu Mao, Gui-Fang Jin, Chao-Yue Qin, Qian-Li Chu, Chang-Ming Hu, A convenient preparation of octafluoro[2,2]paracyclophane and dodecafluoro[2,2]paracyclophane, Tetrahedron Letters, 2002, p. 669-671, 43.

William R. Dolbier, Jr., Jian-Xin Duan, Alex J. Roche, A Novel, Non-High-Dilution Method for Preparation of 1,1,2,2,9,9,10,10-Octafluoro[2.2]paracyclophane, Organic Letters, 2000, p. 1867-1869, 2(13).

*Primary Examiner* — Robert Havlin
(74) *Attorney, Agent, or Firm* — Bacon & Thomas, PLLC

(57) ABSTRACT

The present invention disclosed a preparation method of parylene AF4, which provides a reactant and a reducing agent with the use of catalyst or exposure to UV light with photo-initiator, to shorten the reaction time as a result of minimized the byproduct(s) formation, and obtain high purity (>99.0%) of parylene AF4 product under high concentrated reaction mixture.

17 Claims, No Drawings

CATALYTIC OR PHOTOCATALYTIC PREPARATION METHOD OF PARYLENE AF4

CROSS REFERENCE TO RELATED APPLICATIONS

This application is a divisional of U.S. patent application Ser. No. 13/623,926, filed Sep. 21, 2012, which claims benefit to Taiwanese Application No. 101125578, filed Jul. 6, 2012, the entire contents of which are incorporated herein by reference.

BACKGROUND OF THE INVENTION

1. Field of the Invention

The present invention relates to a preparation method of octafluoro-(2,2)-paracyclophane (parylene AF4) and, more particularly, the present invention relates to a catalytic or a photocatalytic preparation method of parylene AF4.

2. Description of Related Art

By using the vacuum pyrolysis chemical vapor deposition (CVD) method, parylene can be made into an extremely thin film which has an excellent uniformity, chemical stability and high transparency. Parylene is widely used in the forms of coating thin film, for application on the electrical isolation of printed circuit board, moisture protection of sensors or medical equipment, insulating layers of electrical unit, various protective films or packing materials, and preventing corrosion of metal coatings.

Recently, due to high melting point (about 450° C.) and low dielectric constant (about 2.2) of the fluorinated parylene polymers, such as poly(tetraflouro-para-xylene) (parylene HT), with its structure shown in formula (1), compared to the traditional parylene N, parylene C, and parylene D, it has superior anti-UV properties, aging resistance, and thermal stability.

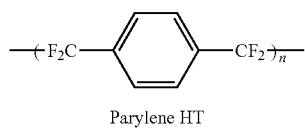

Parylene HT (1)

In addition, parylene HT can be coated on various irregular substrates' surface, for example, glass, metal, resin, plastic, ceramic and paper. The products coated with parylene HT usually have excellent anti-corrosion, anti-moisture, and insulation protection performance, with the advantages of ultra-thin, transparent, and pinholes free, parylene HT can be used in electronic units, automotive industries, solar energy industries, and the low dielectric constant films of semiconductor industries. Currently, the coating of parylene HT is prepared via CVD process. During the CVD process, free radical monomers are produced and then polymerized into parylene HT on the surface of the object: the method is different from the other general preparation via liquid coating methods (such as dip-coating, spray-coating, sputter-coating, and plasma-coating). The coating process first includes the vaporization of fluorinated parylene dimer, such as parylene AF4 (formula (2)); then forming fluorinated para-xylene radicals by high-temperature pyrolysis; finally deposited on the coated substrate; and polymerized to poly(tetraflouro-para-xylene), which is commonly named parylene HT, as shown in formula (1), on the surface of the coated object.

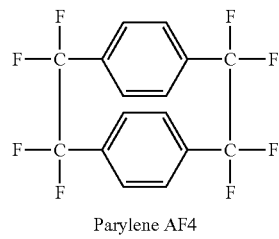

Parylene AF4

(2)

The mechanism of the parylene AF4 polymerized to parylene HT via CVD is shown in formula (3).

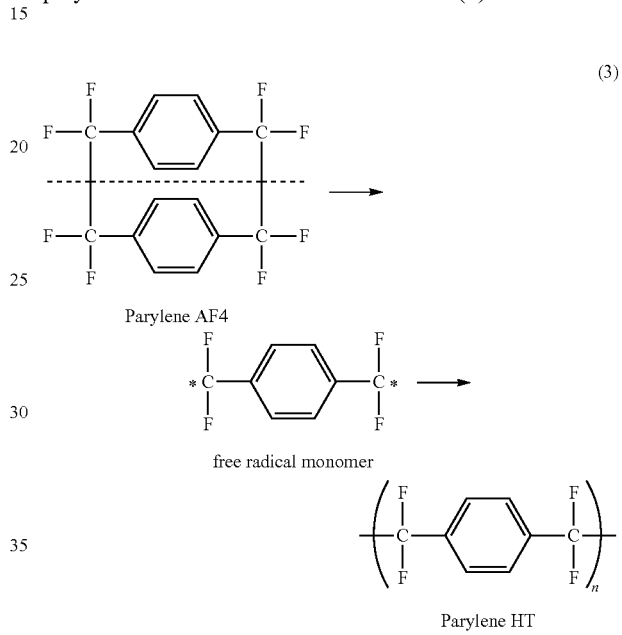

(3)

Many synthetic methods of parylene AF4 has been published in the literature, which mainly use 1,4-bis(chlorodifluoromethyl)benzene (CFB), shown in formula (4), to react with reducing agent Zinc (Zn) and obtain the parylene AF4. In the previous methods, however, in order to prevent the undesired byproducts formation, the reactions were usually carried out in highly diluted conditions, that is, large amount of solvents are necessary in the synthetic methods, therefore, the purchase and storage of the solvent, the process of feeding and the removal of the solvent or impurities will increase the cost of the preparation, coupled with long reaction time, more byproducts and complication of parylene AF4 purification procedure, those methods are not suitable for mass productions.

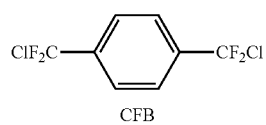

CFB (4)

Therefore, there is a need for the development of a parylene AF4 (octafluoro-[2,2]-paracyclophane) preparation method characterized by high reactant concentration, short reaction time, low cost, less byproducts, easy purification, good reproducibility and stable yield.

SUMMARY OF THE INVENTION

The present invention provides a preparation method for synthesizing parylene AF4 (octafluoro-[2,2]-paracyclophane) using catalyst or photocatalytic, which can reduce the reaction time and increase the yield of parylene AF4 by high concentrated reaction mixture.

In order to achieve the objective, the preparation method of using catalyst of the present invention includes: (A) providing a reactant, a reducing agent, and a catalyst, wherein the reactant is at least one selected from the group consisting of 1,4-bis(chlorodifluoromethyl)benzene (CFB), 1,4-bis(bromodifluoromethyl)benzene (BFB), and 1,4-bis(iododifluoromethyl)benzene (IFB); the reducing agent is at least one selected from the group consisting of zinc, nickel, lead, aluminum, copper, magnesium and tin; and the catalyst is at least one selected from the group consisting of (1) an alkali metal salt, an alkali metal oxide, an alkali metal peroxide, an alkali metal hydroxide, and an alkali metal amide; (2) an alkali earth metal salt, an alkali earth metal oxide, and an alkali earth metal hydroxide; (3) a transition metal salt, a transition metal oxide, a transition metal hydroxide, and a transition metal salt containing hydrate; (4) an amphoteric element salt, an amphoteric element oxide, an amphoteric element hydroxide, an amphoteric element peroxide, and an amphoteric element salt containing hydrate; (5) a non-metallic element acid, and a non-metallic element oxide; (6) a halogen; (7) a phase transfer catalyst of quaternary ammonium salt, a phase transfer catalyst of quaternary phosphonium salt, and a phase transfer catalyst of crown ether; (B) forming a mixture by adding the reactant, the reducing agent, and the catalyst into an aprotic polar solvent; (C) heating the mixture to obtain the parylene AF4 (octafluoro-[2,2]-paracyclophane).

The other preparation method of photocatalytic reaction of the present invention includes: (A) providing a reactant, and a reducing agent, wherein the reactant is at least one selected from the group consisting of 1,4-bis(chlorodifluoromethyl)benzene, 1,4-bis(bromodifluoromethyl)benzene, and 1,4-bis(iododifluoromethyl)benzene; the reducing agent is at least one selected from the group consisting of zinc, nickel, lead, aluminum, copper, magnesium and tin; (B) forming a mixture by adding the reactant and the reducing agent into an aprotic polar solvent; (C) providing an UV light source and heating the mixture to obtain the parylene AF4 (octafluoro-[2,2]-paracyclophane). Wherein, the step (B) of the above further comprises at least a photoinitiator, which is at least one selected from the group consisting of diazo compounds, peroxides, anthraquinones, phosphine oxides, and ketones.

According to the preparation method of the present invention, the reactant may be single component of CFB, BFB, or IFB; or two-component mixture of CFB and BFB, CFB and IFB, or BFB and IFB; or three-component mixture of CFB, BFB and IFB.

According to the preparation method of the present invention, wherein in step (B), the electrochemical potential of the reducing agent must be of the value between 0.45~2.5 eV, and the reducing agent is at least one selected from the group consisting of zinc, nickel, lead, aluminum, copper, magnesium and tin, wherein zinc is preferable. The weight ratio of the reducing agent to the reactant is 1:1~5, wherein 1:1.23.0 is preferable.

In the method according to the present invention, the aprotic polar solvent in step (B) is at least one selected from the group consisting of N,N-dimethylacetamide (DMAC), dimethylsulfoxide (DMSO), dimethylformamide (DMF), tetrahydrofurane (THF), N-methylpyrrolidone (NMP), and acetonitrile (AN), wherein DMAC is preferable. The weight ratio of the reactant to the solvent is 1:1~30, wherein 1:1.5~10 is preferable.

The method of using catalyst according to the present invention, wherein the catalyst used in step (B) is at least one selected from the group consisting of (1) an alkali metal salt, an alkali metal oxide, an alkali metal peroxide, an alkali metal hydroxide, an alkali metal amide; (2) an alkali earth metal salt, an alkali earth metal oxide, an alkali earth metal hydroxide; (3) a transition metal salt, a transition metal oxide, a transition metal hydroxide, a transition metal salt containing hydrate; (4) an amphoteric element salt, an amphoteric element oxide, an amphoteric element hydroxide, an amphoteric element peroxide, an amphoteric element salt containing hydrate; (5) a non-metallic element acid, a non-metallic element oxide; (6) a halogen; (7) a phase transfer catalyst of quaternary ammonium salt, a phase transfer catalyst of quaternary phosphonium salt, and a phase transfer catalyst of crown ether; wherein (1) the alkali metal salt are preferred to be alkali metal halide salt, alkali metal sulfate, alkali metal carbonate, alkali metal acetate, alkali metal nitrate, alkali metal amine salt, alkali metal organic salt, alkali metal phosphite, alkali metal persulfate, and alkali metal oxalate, wherein $CF_3COOLi$, $LiNH_2$, $KH_2PO_3$, KF, KCl, KBr, KI, $CH_3COOK$, $K_2SO_4$, potassium hydrogen phthalate (KHP), potassium tert-butoxide, $Na_2SO_4$, $K_2S_2O_8$, $K_2CO_3$, potassium acrylate, NaCl, NaI, $Na_2CO_3$, $NaNH_2$, $CH_3COONa$, $C_2H_5ONa$, $C_6H_5COONa$, $CH_3ONa$, $C_6H_4(OH)COONa$, sodium oxalate, and CsF are more preferable, wherein $CF_3COOLi$, $LiNH_2$, $KH_2PO_3$, KF, KCl, KBr, KI, $K_2SO_4$, $K_2S_2O_8$, potassium acrylate, NaCl, NaI, $Na_2SO_4$, $NaNH_2$, $CH_3COONa$, $CH_3ONa$, sodium oxalate, and $Na_2CO_3$ are most preferable; the alkali metal oxide is preferred to be $Na_2O$; and the alkali metal peroxide is preferred to be $Na_2O_2$; the alkali metal hydroxide are preferred to be LiOH, and NaOH; wherein NaOH is more preferable; the alkali metal amide is preferred to be potassium phthalimide; (2) the alkali earth metal salt are preferred to be alkali earth metal halide salt, alkali earth metal sulfate, alkali earth metal carbonate, and alkali earth metal nitrate, wherein $CaCl_2$, $CaCO_3$, $CaSO_4$, $MgCl_2$, $MgSO_4$, $MgCO_3$, $Ba(NO_3)_2$ and $BaCl_2$ are more preferable, wherein $CaCl_2$, $CaCO_3$, $MgCl_2$, $MgSO_4$, $MgCO_3$, and $BaCl_2$ are most preferable; the alkali earth metal oxide are preferred to be MgO and CaO; the alkali earth metal hydroxide is preferred to be $Ca(OH)_2$; (3) the transition metal salt are preferred to be transition metal halide salt, transition metal acetate, transition metal sulfate, transition metal nitrate, and transition metal carbonate, wherein $Ag_2SO_4$, $NiCl_2$, $NiCO_3$, $CuI_2$, $ZnSO_4$, and $ZnCl_2$ are more preferable, wherein $CuI_2$ is most preferable; the transition metal oxide is preferred to be ZnO; the transition metal salt containing hydrate are preferred to be $Zn(NO_3)_2.6H_2O$, $Zn(CH_3COO)_2.2H_2O$, $Fe(NO_3)_3.9H_2O$, $FeCl_3.6H_2O$, $MnSO_4.H_2O$, $CuCl_2.2H_2O$, $Cu(NO_3)_2.2.5H_2O$, and $CoCl_2.6H_2O$, wherein $Zn(NO_3)_2.6H_2O$, $MnSO_4.H_2O$, and $Cu(NO_3)_2.2.5H_2O$ are more preferable; (4) the amphoteric element salt are preferred to be amphoteric element halide salt, amphoteric element sulfate, and amphoteric element nitrate, wherein $PbCl_2$, $Pb(NO_3)_2$, and $SnCl_2$ are more preferable; the amphoteric element oxide are preferred to be PbO and $Pb_3O_4$; the amphoteric element hydroxide is preferred to be $Al(OH)_3$; the amphoteric element salt containing hydrate are preferred to be $Pb(CH_3COO)_2.3H_2O$ and $Al(NO_3)_3.9H_2O$, wherein $Pb(CH_3COO)_2.3H_2O$ is more preferable; (5) the non-metallic element acid is preferred to be boric acid; the non-metallic element oxide is preferred to be $P_2O_5$; (6) the halogen are preferred to be bromine ($Br_2$) and iodine ($I_2$); (7) the phase transfer catalyst of quaternary ammonium salt are preferred to be tetramethyl ammonium chloride (PTC-A$_1$), phenyl trimethyl ammonium chloride (PTC-A$_2$), and benzyl triethyl ammonium chloride (PTC-A$_3$), wherein PTC-A$_1$ and PTC-A$_2$ are more preferable; the phase transfer catalyst of quaternary phosphonium salt are preferred to be tetraphenyl phosphonium bromide (PTC-B$_1$) and methyl triphenyl phosphonium bromide (PTC-B$_2$), wherein PTC-B$_1$ is more preferable; and the phase transfer catalyst of crown ether are preferred to be 18-crown-6-ether, 12-crown-4-ether, and 15-crown-5-ether, wherein 18-crown-6-ether is more preferable. The weight ratio of catalyst to reactant is 1:10~500. In order to shorten the reaction time, the dimerization can be accelerated by adding catalyst and also decreasing the undesired byproducts formation.

The method according to the present invention, wherein in step (C), the reaction temperature is 50~250° C., 80~200° C. is preferred, and 100~135° C. is more preferable.

The method of using catalyst according to the present invention, wherein in step (C), the reaction time is 1~24 hour, and 1~12 hour is preferable.

In the method of photocatalytic reaction according to the present invention, step (B) further comprises a photo-initiator, and the photo-initiator is at least one selected from the group consisting of diazo compounds such as azobisisobutyronitrile (AIBN); peroxides such as benzoyl peroxide (BPO); anthraquinones such as 2-ethylanthraquinone (EAQ); phosphine oxides such as diphenyl-(2,4,6-trimethylbenzoyl)phosphine oxide (DTBPO); and ketones such as 1-hydroxy-cyclohexyl phenyl ketone (HCPK), 2-hydroxy-2-methyl-1-phenyl-1-propanone (HMPP), benzyl-α,α-dimethyl ketal (BDK) and 2-methyl-1-[4-(methylthio)phenyl]-2-morpholino-propan-1-one (MPMPO), wherein the weight ratio of the photo-initiator to the reactant is 1:10~100, and 1:30~60 is more preferable.

The method of preparing parylene AF4 of the present invention, by adding at least a reactant selected from the group of CFB, BFB, and IFB into a small amount of solvent combined with a reducing agent to form a highly concentrated reaction mixture, catalyzed by adding catalyst or photocatalytic reaction with photo-initiator, and accelerated the reaction by heating to obtain parylene AF4. The capacity of parylene AF4 production is significantly increased by the high concentrated reaction mixture, therefore, the large scale of parylene AF4 manufacture promises great commercial advantages.

DETAILED DESCRIPTION OF THE PREFERRED EMBODIMENT

Embodiment 1

This embodiment involves providing a 250 ml three-necked bottle and purging with nitrogen, then adding 75 ml of DMAC solvent, 15.68 g (0.24 mol) of reducing agent zinc powder, and 0.21 g (3.5 mmol) of catalyst KF, stirred and preheated to 120° C. Then 29.64 g (0.12 mol) of reactant CFB is added dropwise to the reaction bottle, and the reaction temperature is gradually increased to 135° C., the feeding time is about 2 hours and the reaction is continued for 3 hours. The crude product is filtered and washed by DMAC. The double bond-containing byproduct in filtrate is oxidized by potassium permanganate, and the filtrate is concentrated and water is added to the resulting crude solid in order to remove the inorganic substances. The crude solid obtained from filtration and recrystallized in chloroform (CHCl$_3$) to obtain 8.43 g of pure parylene AF4 (purity 99.5%, yield 40.28%).

The parylene AF4 product is confirmed by analysis: the molecular weight of 352.0 g/mol is confirmed by GC/MS analysis, H$^1$NMR is δ 7.1 ppm (s), and F$^{19}$ NMR is δ −118.0 ppm (s).

Embodiment 2

In this embodiment of the present invention, a 250 ml three-necked bottle is provided and purged with nitrogen, then 50 ml of DMAC solvent is added, 7.84 g (0.12 mol) of reducing agent zinc powder, and 0.10 g (0.6 mmol) of catalyst KI, stirred and preheated to 120° C. Then the mixture of 14.82 g (0.06 mol) of reactant CFB and 1.95 g (0.006 mol) of reactant BFB is added dropwise to the reaction bottle, and the reaction temperature is gradually increased to 140° C., the feeding time is about 1 hour and the reaction is continued for 3 hours. The crude product is purified and analyzed by the same methods of embodiment 1 and 3.58 g of parylene AF4 is obtained (purity 99.63%, yield 31.0%).

Embodiment 3

Provide a 250 ml three-necked bottle and purge with nitrogen, then add 150 ml of DMSO solvent, 7.84 g (0.12 mol) of reducing agent zinc powder, and 0.10 g (0.6 mmol) of catalyst KI, stirred and preheated to 120° C. Then 14.82 g (0.06 mol) of reactant CFB is added dropwise to the reaction bottle, and the reaction temperature is gradually increased to 131° C., the feeding time is about 1 hour and the reaction is continued for 3 hours. The crude product is purified and analyzed by the same methods of embodiment 1 and parylene AF4 is obtained with 99.34% of purity and 26.7% of yield.

Embodiment 4

Provide a 1000 ml three-necked bottle and purge with nitrogen, then add 300 ml of DMAC solvent, 125.4 g (1.92 mol) of reducing agent zinc powder, and 1.9 g (11.4 mmol) of catalyst KI, stirred and preheated to 120° C. Then 237.0 g (0.96 mol) of reactant CFB is added dropwise to the reaction bottle, and the reaction temperature is gradually increased to 142° C., the feeding time is about 3 hours and the reaction is continued for 3 hours. The crude product is purified and analyzed by the same methods of embodiment 1 and 77.2 g of parylene AF4 is obtained (purity 99.7%, yield 45.7%).

Embodiment 5

Provide a 250 ml three-necked bottle and purge with nitrogen, then add 75 ml of DMAC solvent, 15.68 g (0.24 mol) of reducing agent zinc powder, and 0.2 g (3.4 mmol) of catalyst NaCl, stirred and preheated to 120° C. Then 29.64 g (0.12 mol) of reactant CFB is added dropwise to the reaction bottle, and the reaction temperature is gradually increased to 135° C., the feeding time is about 2 hours and the reaction is continued for 2 hours. The crude product is purified and analyzed by the same methods of embodiment 1 and 7.9 g of parylene AF4 is obtained (purity 99.52%, yield 37.44%).

Embodiment 6

Provide a 250 ml three-necked bottle and purge with nitrogen, then add 75 ml of DMAC solvent, 15.68 g (0.24 mol) of reducing agent zinc powder, and 0.2 g (1.4 mmol) of catalyst sodium sulfate (Na$_2$SO$_4$), stirred and preheated to 120° C. Then 29.64 g (0.12 mol) of reactant CFB is added dropwise to the reaction bottle, and the reaction temperature is gradually increased to 134° C., the feeding time is about 2 hours and the reaction is continued for 2 hours. The crude product is purified and analyzed by the same methods of embodiment 1 and 7.74 g of parylene AF4 is obtained (purity 99.66%, yield 36.7%).

Embodiment 7

This embodiment involves to providing a 250 ml three-necked bottle and purging with nitrogen, then adding 50 ml of DMAC solvent, 7.84 g (0.12 mol) of reducing agent zinc powder, and 0.63 g (15.8 mmol) of catalyst sodium hydroxide (NaOH), stirred and preheated to 120° C. Then 14.82 g (0.06 mol) of reactant CFB is added dropwise to the reaction bottle, and the reaction temperature is gradually increased to 130° C., the feeding time is about 1 hour and the reaction is continued for 3 hours. The crude product is purified and analyzed by the same methods of embodiment 1 and 3.7 g of parylene AF4 is obtained (purity 99.28%, yield 35.24%).

Embodiment 8

A 250 ml three-necked bottle is provided and purged with nitrogen, then added with 50 ml of DMAC solvent, 7.84 g (0.12 mol) of reducing agent zinc powder, and 0.10 g (2.5 mmol) of catalyst MgO, stirred and preheated to 120° C. Then 14.82 g (0.06 mol) of reactant CFB is added dropwise to the reaction bottle, and the reaction temperature is gradually increased to 130° C., the feeding time is about 1 hour and the reaction is continued for 2 hours. The crude product is purified and analyzed by the same methods of embodiment 1 and parylene AF4 is obtained with 99.39% of purity and 30.10% of yield.

Embodiment 9

Provide a 250 ml three-necked bottle and purge with nitrogen, then add 75 ml of DMAC solvent, 15.68 g (0.24 mol) of reducing agent zinc powder, and 0.20 g (1.8 mmol) of catalyst $CaCl_2$, stirred and preheated to 120° C. Then 29.64 g (0.12 mol) of reactant CFB is added dropwise to the reaction bottle, and the reaction temperature is gradually increased to 132° C., the feeding time is about 2 hours and the reaction is continued for 2 hours. The crude product is purified and analyzed by the same methods of embodiment 1 and 8.36 g of parylene AF4 is obtained (purity 99.45%, yield 39.81%).

Embodiment 10

Provide a 250 ml three-necked bottle and purge with nitrogen, then add 50 ml of DMAC solvent, 7.84 g (0.12 mol) of reducing agent zinc powder, and 0.10 g (0.59 mmol) of catalyst $MnSO_4.1H_2O$, stirred and preheated to 120° C. Then 14.82 g (0.06 mol) of reactant CFB is added dropwise to the reaction bottle, and the reaction temperature is gradually increased to 140° C., the feeding time is about 1 hour and the reaction is continued for 3 hours. The crude product is purified and analyzed by the same methods of embodiment 1 and parylene AF4 is obtained with 99.59% of purity and 31.43% of yield.

Embodiment 11

Provide a 250 ml three-necked bottle and purge with nitrogen, then add 50 ml of DMAC solvent, 7.84 g (0.12 mol) of reducing agent zinc powder, and 0.10 g (0.32 mmol) of catalyst $CuI_2$, stirred and preheated to 120° C. Then 14.82 g (0.06 mol) of reactant CFB is added dropwise to the reaction bottle, and the reaction temperature is gradually increased to 140° C., the feeding time is about 1 hour and the reaction is continued for 3 hours. The crude product is purified and analyzed by the same methods of embodiment 1 and parylene AF4 is obtained with 99.37% of purity and 30.6% of yield.

Embodiment 12

Provide a 250 ml three-necked bottle and purge with nitrogen, then add 50 ml of DMAC solvent, 7.84 g (0.12 mol) of reducing agent zinc powder, and 0.20 g (2.5 mmol) of catalyst ZnO, stirred and preheated to 120° C. Then 14.82 g (0.06 mol) of reactant CFB is added dropwise to the reaction bottle, and the reaction temperature is gradually increased to 132° C., the feeding time is about 1 hour and the reaction is continued for 2 hours. The crude product is purified and analyzed by the same methods of embodiment 1 and parylene AF4 is obtained with 99.6% of purity and 31.00% of yield.

Embodiment 13

Provide a 250 ml three-necked bottle and purge with nitrogen, then add 50 ml of DMAC solvent, 7.84 g (0.12 mol) of reducing agent zinc powder, and 0.10 g (1.3 mmol) of catalyst $Al(OH)_3$, stirred and preheated to 120° C. Then 14.82 g (0.06 mol) of reactant CFB is added dropwise to the reaction bottle, and the reaction temperature is gradually increased to 136° C., the feeding time is about 1 hour and the reaction is continued for 3 hours. The crude product is purified and analyzed by the same methods of embodiment 1 and parylene AF4 is obtained with 99.5% of purity and 31.42% of yield.

Embodiment 14

This embodiment of the present invention provides a 250 ml three-necked bottle and is purged with nitrogen, then adding 75 ml of DMAC solvent, 15.68 g (0.24 mol) of reducing agent zinc powder, and 0.28 g (1.0 mmol) of catalyst $PbCl_2$, stirred and preheated to 120° C. Then 29.64 g (0.12 mol) of reactant CFB is added dropwise to the reaction bottle, and the reaction temperature is gradually increased to 130° C., the feeding time is about 2 hours and the reaction is continued for 2 hours. The crude product is purified and analyzed by the same methods of embodiment 1 and 7.6 g of parylene AF4 is obtained with 99.46% of purity and 36.2% of yield.

Embodiment 15

Provide a 250 ml three-necked bottle and purge with nitrogen, then add 75 ml of DMAC solvent, 15.68 g (0.24 mol) of reducing agent zinc powder, and 0.20 g (0.53 mmol) of catalyst $Pb(CH_3COO)_2.3H_2O$, stirred and preheated to 120° C. Then 29.64 g (0.12 mol) of reactant CFB is added dropwise to the reaction bottle, and the reaction temperature is gradually increased to 134° C., the feeding time is about 2 hours and the reaction is continued for 3 hours. The crude product is purified and analyzed by the same methods of embodiment 1 and 6.63 g of parylene AF4 is obtained with 99.3% of purity and 31.4% of yield.

Embodiment 16

Provide a 250 ml three-necked bottle and purge with nitrogen, then add 75 ml of DMAC solvent, 15.68 g (0.24 mol) of reducing agent zinc powder, and 0.30 g (2.7 mmol) of catalyst PTC-A₁, stirred and preheated to 120° C. Then 29.64 g (0.12 mol) of reactant CFB is added dropwise to the reaction bottle, and the reaction temperature is gradually increased to 136° C., the feeding time is about 2 hours and the reaction is continued for 3 hours. The crude product is purified and analyzed by the same methods of embodiment 1 and 8.6 g of parylene AF4 is obtained with 99.45% of purity and 40.76% of yield.

Embodiment 17

Provide a 250 ml three-necked bottle and purge with nitrogen, then add 75 ml of DMAC solvent, 15.68 g (0.24 mol) of reducing agent zinc powder, and 0.50 g (1.4 mmol) of catalyst PTC-B$_2$, stirred and preheated to 120° C. Then 29.64 g (0.12 mol) of reactant CFB is added dropwise to the reaction bottle, and the reaction temperature is gradually increased to 140° C., the feeding time is about 2 hours and the reaction is continued for 3 hours. The crude product is purified and analyzed by the same methods of embodiment 1 and 7.53 g of parylene AF4 is obtained with 99.61% of purity and 35.7% of yield.

Embodiment 18

Provide a 250 ml three-necked bottle and purge with nitrogen, then add 75 ml of DMAC solvent, 15.68 g (0.24 mol) of reducing agent zinc powder, and 0.40 g (1.5 mmol) of catalyst 18-crown-6, stirred and preheated to 120° C. Then 29.64 g (0.12 mol) of reactant CFB is added dropwise to the reaction bottle, and the reaction temperature is gradually increased to 136° C., the feeding time is about 2 hours and the reaction is continued for 3 hours. The crude product is purified and analyzed by the same methods of embodiment 1 and 8.04 g of parylene AF4 is obtained with 99.72% of purity and 38.1% of yield.

Embodiment 19

Provide a 250 ml three-necked bottle and purge with nitrogen, then add 50 ml of DMAC solvent, 7.84 g (0.12 mol) of reducing agent zinc powder, and 0.30 g (13 mmol) of catalyst LiNH$_2$, stirred and preheated to 120° C. Then 14.82 g (0.06 mol) of reactant CFB is added dropwise to the reaction bottle, and the reaction temperature is gradually increased to 136° C., the feeding time is about 1 hour and the reaction is continued for 3 hours. The crude product is purified and analyzed by the same methods of embodiment 1 and parylene AF4 is obtained with 99.41% of purity and 40.5% of yield.

Embodiment 20

Provide a 250 ml three-necked bottle and purge with nitrogen, then add 50 ml of DMAC solvent, 7.84 g (0.12 mol) of reducing agent zinc powder, and 0.30 g (12.5 mmol) of catalyst LiOH, stirred and preheated to 120° C. Then 14.82 g (0.06 mol) of reactant CFB is added dropwise to the reaction bottle, and the reaction temperature is gradually increased to 136° C., the feeding time is about 1 hour and the reaction is continued for 3 hours. The crude product is purified and analyzed by the same methods of embodiment 1 and parylene AF4 is obtained with 99.52% of purity and 29.8% of yield.

Embodiments 21~100

The preparation methods, reactants, reducing agents, catalysts, solvents and the dosages, reaction temperature, reaction time and the yields of parylene AF4 of embodiments 21~100 are shown in table 1.

Embodiment 101

Provide a 250 ml three-necked bottle and purge with nitrogen, then add 50 ml of DMAC solvent and 7.84 g (0.12 mol) of reducing agent zinc powder, and exposed to UV light, stirred and preheated to 120° C. Then 14.82 g (0.06 mol) of reactant CFB is added dropwise to the reaction bottle, and the reaction temperature is gradually increased to 134° C., the feeding time is about 1 hour and the reaction is continued for 20 hours. The crude product is purified and analyzed by the same methods of embodiment 1 and parylene AF4 is obtained with 99.23% of purity and 33.9% of yield.

Embodiment 102

Provide a 250 ml three-necked bottle and purge with nitrogen, then add 50 ml of DMAC solvent, 7.84 g (0.12 mol) of reducing agent zinc powder, and 0.30 g (1.83 mmol) of photo-initiator AIBN and then exposed to UV light, stirred and preheated to 120° C. Then 14.82 g (0.06 mol) of reactant CFB is added dropwise to the reaction bottle, and the reaction temperature is gradually increased to 132° C., the feeding time is about 1 hour and the reaction is continued for 3 hours. The crude product is purified and analyzed by the same methods of embodiment 1 and parylene AF4 is obtained with 99.31% of purity and 33.3% of yield.

Embodiments 103~115

The preparation methods of embodiments 103~115 are the same as embodiment 102, and their reactants, reducing agents, photo-initiators, solvents and the dosages, reaction temperature, reaction time and the yields of parylene AF4 of embodiments 103~115 are shown in table 2.

Comparative Example 1

Provide a 250 ml three-necked bottle and purge with nitrogen, then add 100 ml of DMAC solvent, and 31.36 g (0.48 mol) of reducing agent zinc powder, stirred and preheated to 120° C. Then 59.28 g (0.24 mol) of reactant CFB is added dropwise to the reaction bottle, and the reaction temperature is gradually increased to 130° C., the feeding time is about 2 hours and the reaction is continued for 26 hours. The crude product is purified and analyzed by the same methods of embodiment 1 and 14.50 g of parylene AF4 is obtained with 99.33% of purity and 34.5% of yield.

Comparative Example 2

Provide a 250 ml three-necked bottle and purge with nitrogen, then add 50 ml of DMAC solvent, 3.24 g (0.12 mol) of reducing agent aluminum powder, and 0.10 g (0.6 mmol) of catalyst KI, stirred and preheated to 120° C. Then 14.82 g (0.06 mol) of reactant CFB is added dropwise to the reaction bottle, and the reaction temperature is gradually increased to 138° C., the feeding time is about 1 hour and the reaction is continued for 3 hours. The crude product is purified and analyzed by the same methods of embodiment 1 and parylene AF4 is obtained with 99.45% of purity and 11.8% of yield.

Comparative Example 3

A 250 ml three-necked bottle is provided and purged with nitrogen, then adding 150 ml of AN solvent, 7.84 g (0.12 mol) of reducing agent zinc powder, and 0.10 g (0.6 mmol) of catalyst KI, stirred and preheated to 80° C. Then 14.82 g (0.06 mol) of reactant CFB is added dropwise to the reaction bottle, and the reaction temperature is gradually increased to 82.5° C., the feeding time is about 1 hour and the reaction is continued for 20 hours. The crude product is purified and analyzed by the same methods of embodiment 1 and 1.06 g of parylene AF4 is obtained with 99.64% of purity and 10.05% of yield.

Comparative Example 4

Provide a 250 ml three-necked bottle and purge with nitrogen, then add 100 ml of DMAC solvent, and 15.68 g (0.24 mol) of reducing agent Zinc powder, and exposed to UV light, stirred and preheated to 120° C. Then 29.64 g (0.12 mol) of reactant CFB is added dropwise to the reaction bottle, and the reaction temperature is gradually increased to 130° C., the feeding time is about 2 hour and the reaction is continued for 20 hours. The crude product is purified and analyzed by the same methods of embodiment 1 and parylene AF4 is obtained with 99.68% of purity and 35.7% of yield.

TABLE 1

The parylene AF4 preparation enhanced by catalyst.

$$\text{Reactant (R) + Reducing Agent (RA)} \xrightarrow[\text{solvent (S)}]{\text{catalyst (X)}} \text{Parylene AF4}$$

| Embodiment | Reactant (R) (g/mol) | Reducing agent (RA) (g/mol) | Catalyst (X) (g/mmol) | Solvent (S) (ml) | Reaction temperature (° C.) Initial/End | Reaction time (hr) Feed/End | Parylene AF4 yield (%) |
|---|---|---|---|---|---|---|---|
| 1 | CFB 29.64/0.12 | Zn 15.68/0.24 | KF 0.21/3.5 | DMAC 75 | 120/135 | 2/3 | 40.28 |
| 2 | CFB 14.82/0.06 BFB 1.95/0.006 | Zn 7.84/0.12 | KI 0.1/0.6 | DMAC 50 | 120/140 | 1/3 | 31.0 |
| 3 | CFB 14.82/0.06 | Zn 7.84/0.12 | KI 0.1/0.6 | DMSO 150 | 120/131 | 1/3 | 26.7 |
| 4 | CFB 237.0/0.96 | Zn 125.4/1.92 | KI 1.9/11.4 | DMAC 300 | 120/142 | 3/3 | 45.7 |
| 5 | CFB 29.64/0.12 | Zn 15.68/0.24 | NaCl 0.2/3.4 | DMAC 75 | 120/135 | 2/2 | 37.44 |
| 6 | CFB 29.64/0.12 | Zn 15.68/0.24 | $Na_2SO_4$ 0.2/1.4 | DMAC 75 | 120/134 | 2/2 | 36.7 |
| 7 | CFB 14.82/0.06 | Zn 7.84/0.12 | NaOH 0.63/15.8 | DMAC 50 | 120/130 | 1/3 | 35.24 |
| 8 | CFB 14.82/0.06 | Zn 7.84/0.12 | MgO 0.1/2.5 | DMAC 50 | 120/130 | 1/2 | 30.1 |
| 9 | CFB 29.64/0.12 | Zn 15.68/0.24 | $CaCl_2$ 0.2/1.8 | DMAC 75 | 120/132 | 2/2 | 39.81 |
| 10 | CFB 14.82/0.06 | Zn 7.84/0.12 | $MnSO_4 \cdot 1H_2O$ 0.1/0.59 | DMAC 50 | 120/140 | 1/3 | 31.43 |
| 11 | CFB 14.82/0.06 | Zn 7.84/0.12 | $CuI_2$ 0.1/0.32 | DMAC 50 | 120/140 | 1/3 | 30.6 |
| 12 | CFB 14.82/0.06 | Zn 7.84/0.12 | ZnO 0.2/2.5 | DMAC 50 | 120/132 | 1/2 | 31.0 |
| 13 | CFB 14.82/0.06 | Zn 7.84/0.12 | $Al(OH)_3$ 0.1/1.3 | DMAC 50 | 120/136 | 1/3 | 31.42 |
| 14 | CFB 29.64/0.12 | Zn 15.68/0.24 | $PbCl_2$ 0.28/1.0 | DMAC 75 | 120/130 | 2/2 | 36.2 |
| 15 | CFB 29.64/0.12 | Zn 15.68/0.24 | $Pb(CH_3COO)_2 \cdot 3H_2O$ 0.2/0.53 | DMAC 75 | 120/134 | 2/3 | 31.4 |
| 16 | CFB 29.64/0.12 | Zn 15.68/0.24 | PTC-$A_1$ 0.3/2.7 | DMAC 75 | 120/136 | 2/3 | 40.76 |
| 17 | CFB 29.64/0.12 | Zn 15.68/0.24 | PTC-$B_2$ 0.5/1.4 | DMAC 75 | 120/140 | 2/3 | 35.7 |
| 18 | CFB 29.64/0.12 | Zn 15.68/0.24 | 18-crown-6 0.4/1.5 | DMAC 75 | 120/136 | 2/3 | 38.1 |
| 19 | CFB 14.82/0.06 | Zn 7.84/0.12 | $LiNH_2$ 0.3/13 | DMAC 50 | 120/136 | 1/3 | 40.5 |
| 20 | CFB 14.82/0.06 | Zn 7.84/0.12 | LiOH 0.3/12.5 | DMAC 50 | 120/136 | 1/3 | 29.8 |
| 21 | CFB 14.82/0.06 | Zn 7.84/0.12 | $CF_3CO_2Li$ 0.3/2.5 | DMAC 50 | 120/136 | 1/3 | 33.7 |
| 22 | CFB 29.64/0.12 | Zn 15.68/0.24 | KF 0.3/5.2 | DMAC 75 | 120/132 | 2/2 | 37.91 |
| 23 | BFB 20.16/0.06 | Zn 7.84/0.12 | KF 0.1/1.7 | DMAC 50 | 120/136 | 1/2 | 31.0 |
| 24 | CFB 14.82/0.06 BFB 1.95/0.006 | Zn 7.84/0.12 | KF 0.1/1.7 | DMAC 50 | 120/140 | 1/3 | 24.5 |
| 25 | CFB 14.82/0.06 | Zn 7.84/0.12 | KF 0.1/1.7 | DMAC 50 | 60/140 | 1/3 | 27.0 |

TABLE 1-continued

The parylene AF4 preparation enhanced by catalyst.

$$\text{Reactant (R)} + \text{Reducing Agent (RA)} \xrightarrow[\text{solvent (S)}]{\text{catalyst (X)}} \text{Parylene AF4}$$

| Embodiment | Reactant (R) (g/mol) | Reducing agent (RA) (g/mol) | Catalyst (X) (g/mmol) | Solvent (S) (ml) | Reaction temperature (° C.) Initial/End | Reaction time (hr) Feed/End | Parylene AF4 yield (%) |
|---|---|---|---|---|---|---|---|
| 26 | CFB 29.64/0.12 | Zn 15.68/0.24 | KCl 0.2/2.7 | DMAC 75 | 120/135 | 2/2 | 33.18 |
| 27 | CFB 29.64/0.12 | Zn 15.68/0.24 | Br 0.2/1.7 | DMAC 75 | 120/132 | 2/2 | 35.55 |
| 28 | CFB 29.64/0.12 | Zn 15.68/0.24 | KI 0.5/3.0 | DMAC 75 | 120/126 | 2/2 | 32.7 |
| 29 | BFB 20.16/0.06 | Zn 7.84/0.12 | KI 0.1/0.6 | DMAC 50 | 120/136 | 1/2 | 32.0 |
| 30 | CFB 14.82/0.06 | Zn 7.84/0.12 | KI 0.1/0.6 | DMF 150 | 120/131 | 1/3 | 23.8 |
| 31 | CFB 14.82/0.06 | Zn 7.84/0.12 | KI 0.1/0.6 | DMAC 50 | 60/140 | 1/3 | 30.5 |
| 32 | CFB 14.82/0.06 | Zn 7.84/0.12 | KI 0.1/0.6 | DMAC 50 | 80/100 | 1/5 | 26.7 |
| 33 | CFB 14.82/0.06 | Zn 7.84/0.12 | KI 0.1/0.6 | DMAC 50 | 100/120 | 1/5 | 29.2 |
| 34 | CFB 29.64/0.12 | Zn 15.68/0.24 | $K_2CO_3$ 0.2/1.45 | DMAC 75 | 120/134 | 2/2 | 29.5 |
| 35 | CFB 29.64/0.12 | Zn 15.68/0.24 | $K_2SO_4$ 0.2/1.15 | DMAC 75 | 120/134 | 2/2 | 32.6 |
| 36 | CFB 14.82/0.06 | Zn 7.84/0.12 | $KH_2PO_3$ 0.1/0.83 | DMAC 50 | 120/140 | 1/2 | 36.2 |
| 37 | CFB 29.64/0.12 | Zn 15.68/0.24 | $K_2S_2O_8$ 0.2/0.74 | DMAC 75 | 120/136 | 2/3 | 33.3 |
| 38 | CFB 14.82/0.06 | Zn 7.84/0.12 | $CH_3COOK$ 0.3/3.1 | DMAC 50 | 120/135 | 1/3 | 28.1 |
| 39 | CFB 14.82/0.06 | Zn 7.84/0.12 | KHP 0.1/0.5 | DMAC 50 | 120/136 | 1/3 | 27.9 |
| 40 | CFB 29.64/0.12 | Zn 15.68/0.24 | NaCl 0.5/8.5 | DMAC 75 | 120/138 | 2/1 | 34.12 |
| 41 | CFB 29.64/0.12 | Zn 15.68/0.24 | NaI 0.2/1.3 | DMAC 75 | 120/135 | 2/2 | 35.55 |
| 42 | CFB 29.64/0.12 | Zn 15.68/0.24 | $Na_2CO_3$ 0.2/1.9 | DMAC 75 | 120/134 | 2/2 | 35.7 |
| 43 | CFB 14.82/0.06 | Zn 7.84/0.12 | $Na_2O$ 0.1/1.6 | DMAC 50 | 120/135 | 1/3 | 32.4 |
| 44 | CFB 14.82/0.06 | Zn 7.84/0.12 | $Na_2O_2$ 0.3/3.85 | DMAC 50 | 120/136 | 1/3 | 37.3 |
| 45 | CFB 14.82/0.06 | Zn 7.84/0.12 | $C_2H_5ONa$ 0.3/4.4 | DMAC 50 | 120/136 | 1/3 | 25.8 |
| 46 | CFB 14.82/0.06 | Zn 7.84/0.12 | $CH_3COONa$ 0.3/3.66 | DMAC 50 | 120/135 | 1/3 | 33.3 |
| 47 | CFB 14.82/0.06 | Zn 7.84/0.12 | $C_6H_5COONa$ 0.3/2.1 | DMAC 50 | 120/136 | 1/3 | 29.5 |
| 48 | CFB 14.82/0.06 | Zn 7.84/0.12 | $CH_3ONa$ 0.3/5.6 | DMAC 50 | 120/136 | 1/3 | 33.8 |
| 49 | CFB 14.82/0.06 | Zn 7.84/0.12 | CsF 0.1/0.66 | DMAC 50 | 120/140 | 1/2 | 29.52 |
| 50 | CFB 29.64/0.12 | Zn 15.68/0.24 | $MgCl_2$ 0.2/2.1 | DMAC 75 | 120/130 | 2/2 | 31.9 |
| 51 | CFB 29.64/0.12 | Zn 15.68/0.24 | $MgSO_4$ 0.2/1.7 | DMAC 75 | 120/132 | 2/2 | 38.39 |
| 52 | CFB 14.82/0.06 | Zn 7.84/0.12 | $MgCO_3$ 0.1/1.2 | DMAC 50 | 120/132 | 1/2 | 33.8 |
| 53 | BFB 20.16/0.06 | Zn 7.84/0.12 | $CaCl_2$ 0.1/0.9 | DMAC 50 | 120/136 | 1/2 | 32.8 |
| 54 | CFB 14.82/0.06 BFB 1.95/0.006 | Zn 7.84/0.12 | $CaCl_2$ 0.1/0.9 | DMAC 50 | 120/140 | 1/3 | 31.4 |
| 55 | CFB 14.82/0.06 | Zn 7.84/0.12 | $CaCl_2$ 0.1/0.9 | DMAC 50 | 60/140 | 1/3 | 28.4 |
| 56 | CFB 29.64/0.12 | Zn 15.68/0.24 | $CaCO_3$ 0.2/2.0 | DMAC 75 | 120/134 | 2/2 | 32.85 |
| 57 | CFB 14.82/0.06 | Zn 7.84/0.12 | $CaSO_4$ 0.1/0.74 | DMAC 50 | 120/132 | 1/2 | 29.5 |

TABLE 1-continued

The parylene AF4 preparation enhanced by catalyst.

$$\text{Reactant (R)} + \text{Reducing Agent (RA)} \xrightarrow[\text{solvent (S)}]{\text{catalyst (X)}} \text{Parylene AF4}$$

| Embodiment | Reactant (R) (g/mol) | Reducing agent (RA) (g/mol) | Catalyst (X) (g/mmol) | Solvent (S) (ml) | Reaction temperature (° C.) Initial/End | Reaction time (hr) Feed/End | Parylene AF4 yield (%) |
|---|---|---|---|---|---|---|---|
| 58 | CFB 14.82/0.06 | Zn 7.84/0.12 | CaO 0.1/1.8 | DMAC 50 | 120/140 | 1/3 | 35.24 |
| 59 | CFB 14.82/0.06 | Zn 7.84/0.12 | Ca(OH)$_2$ 0.3/4.0 | DMAC 50 | 120/130 | 1/2 | 23.14 |
| 60 | CFB 14.82/0.06 | Zn 7.84/0.12 | Ba(NO$_3$)$_2$ 0.1/0.38 | DMAC 50 | 120/136 | 1/3 | 29.52 |
| 61 | CFB 14.82/0.06 | Zn 7.84/0.12 | BaCl$_2$ 0.1/0.48 | DMAC 50 | 120/140 | 1/2 | 34.28 |
| 62 | CFB 14.82/0.06 | Zn 7.84/0.12 | FeCl$_3$•6H$_2$O 0.1/0.37 | DMAC 50 | 120/136 | 1/3 | 25.3 |
| 63 | CFB 14.82/0.06 | Zn 7.84/0.12 | Fe(NO$_3$)$_3$•9H$_2$O 0.1/0.25 | DMAC 50 | 120/136 | 1/2 | 20.0 |
| 64 | CFB 14.82/0.06 | Zn 7.84/0.12 | CoCl$_2$•6H$_2$O 0.1/0.42 | DMAC 50 | 120/140 | 1/2 | 28.6 |
| 65 | CFB 14.82/0.06 | Zn 7.84/0.12 | Co(NO$_3$)$_2$•6H$_2$O 0.1/0.344 | DMAC 50 | 120/140 | 1/3 | 17.8 |
| 66 | CFB 14.82/0.06 | Zn 7.84/0.12 | NiCl$_2$ 0.1/0.77 | DMAC 50 | 120/140 | 1/3 | 10.86 |
| 67 | CFB 29.64/0.12 | Zn 15.68/0.24 | Ni(CH$_3$COO)$_2$•4H$_2$O 0.2/0.8 | DMAC 75 | 120/140 | 2/3 | 18.1 |
| 68 | CFB 14.82/0.06 | Zn 7.84/0.12 | NiCO$_3$ 0.1/0.84 | DMAC 50 | 120/140 | 1/2 | 26.7 |
| 69 | CFB 14.82/0.06 | Zn 7.84/0.12 | Ni—Al—Si 0.5/ | DMAC 50 | 120/140 | 1/2 | 36.6 |
| 70 | CFB 14.82/0.06 | Zn 7.84/0.12 | Ni(NO$_3$)$_2$•6H$_2$O 0.1/0.34 | DMAC 50 | 120/140 | 1/3 | 13.8 |
| 71 | CFB 14.82/0.06 | Zn 7.84/0.12 | CuCl$_2$•2H$_2$O 0.1/0.59 | DMAC 50 | 120/140 | 1/3 | 24.5 |
| 72 | CFB 14.82/0.06 | Zn 7.84/0.12 | CuSO$_4$•5H$_2$O 0.1/0.4 | DMAC 50 | 120/134 | 1/2 | 15.8 |
| 73 | CFB 14.82/0.06 | Zn 7.84/0.12 | Cu(NO$_3$)$_2$•2.5H$_2$O 0.1/0.43 | DMAC 50 | 120/140 | 1/3 | 30.96 |
| 74 | CFB 14.82/0.06 | Zn 7.84/0.12 | ZnCl$_2$ 0.5/3.7 | DMAC 50 | 120/134 | 1/2 | 25.7 |
| 75 | CFB 14.82/0.06 | Zn 7.84/0.12 | ZnSO$_4$ 0.2/1.24 | DMAC 50 | 120/132 | 1/2 | 24.8 |
| 76 | CFB 14.82/0.06 | Zn 7.84/0.12 | Zn(NO$_3$)$_2$•6H$_2$O 0.2/0.68 | DMAC 50 | 120/132 | 1/2 | 30.8 |
| 77 | CFB 14.82/0.06 | Zn 7.84/0.12 | Zn(CH$_3$COO)$_2$•2H$_2$O 0.1/0.46 | DMAC 50 | 120/136 | 1/3 | 25.7 |
| 78 | CFB 14.82/0.06 | Zn 7.84/0.12 | Ag$_2$SO$_4$ 0.1/0.32 | DMAC 50 | 120/134 | 1/2 | 23.8 |
| 79 | CFB 14.82/0.06 | Zn 7.84/0.12 | Al(NO$_3$)$_3$•9H$_2$O 0.2/0.53 | DMAC 50 | 120/140 | 1/2 | 22.3 |
| 80 | CFB 29.64/0.12 | Zn 15.68/0.24 | SnCl$_2$ 0.2/1.0 | DMAC 75 | 120/140 | 2/3 | 20.5 |
| 81 | CFB 29.64/0.12 | Zn 15.68/0.24 | Pb(NO$_3$)$_2$ 0.33/1.0 | DMAC 75 | 120/130 | 2/2 | 26.2 |
| 82 | CFB 29.64/0.12 | Zn 15.68/0.24 | PbO 0.2/0.9 | DMAC 75 | 120/140 | 2/2 | 38.1 |
| 83 | CFB 14.82/0.06 | Zn 7.84/0.12 | Pb$_3$O$_4$ 0.1/0.15 | DMAC 50 | 120/136 | 1/2 | 32.1 |
| 84 | CFB 14.82/0.06 | Zn 7.84/0.12 | (NH$_4$)$_2$SiF$_6$ 0.1/0.56 | DMAC 50 | 120/140 | 1/3 | 33.6 |
| 85 | CFB 14.82/0.06 | Zn 7.84/0.12 | P$_2$O$_5$ 0.1/0.66 | DMAC 50 | 120/140 | 1/2 | 33.5 |
| 86 | CFB 14.82/0.06 | Zn 7.84/0.12 | H$_3$BO$_3$ 0.1/1.6 | DMAC 50 | 120/130 | 1/3 | 32.4 |
| 87 | CFB 29.64/0.12 | Zn 15.68/0.24 | PTC-A$_2$ 0.43/2.5 | DMAC 75 | 120/140 | 2/3 | 35.7 |
| 88 | CFB 29.64/0.12 | Zn 15.68/0.24 | PTC-A$_3$ 0.3/1.4 | DMAC 75 | 120/134 | 2/2 | 23.8 |
| 89 | CFB 29.64/0.12 | Zn 15.68/0.24 | PTC-B$_1$ 0.5/1.2 | DMAC 75 | 120/135 | 2/3 | 37.91 |
| 90 | CFB 14.82/0.06 | Zn 7.84/0.12 | 12-crown-4 0.3/1.7 | DMAC 50 | 120/140 | 1/3 | 32.4 |

TABLE 1-continued

The parylene AF4 preparation enhanced by catalyst.

$$\text{Reactant (R)} + \text{Reducing Agent (RA)} \xrightarrow[\text{solvent (S)}]{\text{catalyst (X)}} \text{Parylene AF4}$$

| Embodiment | Reactant (R) (g/mol) | Reducing agent (RA) (g/mol) | Catalyst (X) (g/mmol) | Solvent (S) (ml) | Reaction temperature (°C.) Initial/End | Reaction time (hr) Feed/End | Parylene AF4 yield (%) |
|---|---|---|---|---|---|---|---|
| 91 | CFB 14.82/0.06 | Zn 7.84/0.12 | 15-crown-5 0.3/1.36 | DMAC 50 | 120/140 | 1/3 | 35.2 |
| 92 | CFB 14.82/0.06 | Zn 7.84/0.12 | $NaNH_2$ 0.3/7.7 | DMAC 50 | 120/135 | 1/3 | 32.95 |
| 93 | CFB 14.82/0.06 | Zn 7.84/0.12 | $C_6H_4(OH)COONa$ 0.3/1.9 | DMAC 50 | 120/135 | 1/3 | 27.6 |
| 94 | CFB 14.82/0.06 | Zn 7.84/0.12 | $C_4H_9KO$ 0.3/2.7 | DMAC 50 | 120/135 | 1/3 | 28.6 |
| 95 | CFB 14.82/0.06 | Zn 7.84/0.12 | $C_3H_3KO_2$ 0.3/2.7 | DMAC 50 | 120/137 | 1/3 | 31.6 |
| 96 | CFB 14.82/0.06 | Zn 7.84/0.12 | $C_2Na_2O_4$ 0.3/2.24 | DMAC 50 | 120/137 | 1/3 | 32.67 |
| 97 | CFB 14.82/0.06 | Zn 7.84/0.12 | $C_8H_4KNO_2$ 0.3/1.62 | DMAC 50 | 120/137 | 1/3 | 27.9 |
| 98 | CFB 14.82/0.06 | Zn 7.84/0.12 | $I_2$ 0.3/1.18 | DMAC 50 | 120/136 | 1/3 | 31.7 |
| 99 | CFB 14.82/0.06 | Zn 7.84/0.12 | $Br_2$ 0.3/1.88 | DMAC 50 | 120/134 | 1/3 | 37.0 |
| 100 | CFB 14.82/0.06 | Zn 7.84/0.12 | HCl (36%) 0.5/5 | DMAC 50 | 120/134 | 1/3 | 18.67 |
| Comparative example 1 | CFB 59.28/0.24 | Zn 31.36/0.48 | none | DMAC 100 | 120/130 | 2/26 | 34.5 |
| Comparative example 2 | CFB 14.82/0.06 | Al 3.24/0.12 | KI 0.1/0.6 | DMAC 50 | 120/138 | 1/3 | 11.8 |
| Comparative example 3 | CFB 14.82/0.06 | Zn 7.84/0.12 | KI 0.1/0.6 | AN 150 | 80/82.5 | 1/20 | 10.05 |

Note:
some abbreviation chemical name is as follows
PTC-$A_1$ Tetramethyl ammonium chloride
PTC-$A_2$ Phenyl trimethyl ammonium chloride
PTC-$A_3$ Benzyl triethyl ammonium hydroxide
PTC-$B_1$ Tetraphenylphosphonium bromide
PTC-$B_2$ Methyl triphenylphosphonium bromide
KHP Potassium hydrogen phthalate
CFB 1,4-bis(chlorodifluoromethyl)Benzene
BFB 1,4-bis(bromodifluoromethyl)Benzene
DMAC N,N-Dimethylacetamide
DMF N,N-Dimethylformamide
DMSO Dimethylsulfoxide
AN Acetonitrile
$C_4H_9KO$ Potassium tert-butoxide
$C_3H_3KO_2$ Potassium acrylate
$C_2Na_2O_4$ Sodium oxalate
$C_8H_4KNO_2$ Potassium phthalimide
$K_2S_2O_8$ Potassium persulfate
Ni—Al—Si Nickel-Nickel Oxide deposited on silica-Alumina XERTEX Dohrmann(German company) product for GC packing column usage

TABLE 2

The parylene AF4 preparation accelerated by UV with photo-initiator $$\text{Reactant (R)} + \text{Reducing Agent (RA)} \xrightarrow[\text{solvent (S)}]{\text{photolysis (P)}} \text{Parylene AF4}$$

| Embodiment | Reactant (R) (g/mol) | Reducing agent (RA) (g/mol) | UV & initiator (P) (g/mmol) | Solvent (S) (ml) | Reaction temperature (°C.) Initial/End | Reaction time (hr) Feed/End | parylene AF4 yield (%) |
|---|---|---|---|---|---|---|---|
| 101 | CFB 14.82/0.06 | Zn 7.84/0.12 | UV | DMAC 50 | 120/134 | 1/20 | 33.9 |
| 102 | CFB 14.82/0.06 | Zn 7.84/0.12 | UV + AIBN 0.3/1.83 | DMAC 50 | 120/132 | 1/3 | 33.3 |

TABLE 2-continued

The parylene AF4 preparation accelerated by UV with photo-initiator $$\text{Reactant (R)} + \text{Reducing Agent (RA)} \xrightarrow[\text{solvent (S)}]{\text{photolysis (P)}} \text{Parylene AF4}$$

| Embodiment | Reactant (R) (g/mol) | Reducing agent (RA) (g/mol) | UV & initiator (P) (g/mmol) | Solvent (S) (ml) | Reaction temperature (°C.) Initial/End | Reaction time (hr) Feed/End | parylene AF4 yield (%) |
|---|---|---|---|---|---|---|---|
| 103 | CFB 14.82/0.06 | Zn 7.84/0.12 | UV + HMPP 0.3/1.83 | DMAC 50 | 120/136 | 1/7 | 37.7 |
| 104 | CFB 14.82/0.06 | Zn 7.84/0.12 | UV + HCPK 0.3/1.47 | DMAC 50 | 120/135 | 1/5 | 32.4 |
| 105 | CFB 14.82/0.06 | Zn 7.84/0.12 | UV + BDK 0.3/1.17 | DMAC 50 | 120/140 | 1/4 | 29.5 |
| 106 | CFB 14.82/0.06 | Zn 7.84/0.12 | UV + BPO 0.3/1.24 | DMAC 50 | 120/140 | 1/4 | 27.7 |
| 107 | CFB 14.82/0.06 | Zn 7.84/0.12 | UV + DTBPO 0.3/0.86 | DMAC 50 | 120/136 | 1/4 | 24.8 |
| 108 | CFB 14.82/0.06 | Zn 7.84/0.12 | UV + MPMPO 0.3/1.07 | DMAC 50 | 120/136 | 1/4 | 36.2 |
| 109 | CFB 14.82/0.06 | Zn 7.84/0.12 | UV + EAQ 0.3/1.27 | DMAC 50 | 120/138 | 1/4 | 36.6 |
| 110 | BFB 20.16/0.06 | Zn 7.84/0.12 | UV + HMPP 0.3/1.83 | DMAC 50 | 120/136 | 1/3 | 36.5 |
| 111 | CFB 14.82/0.06 | Zn 7.84/0.12 | UV + HMPP 0.3/1.83 | DMSO 50 | 120/136 | 1/4 | 25.7 |
| 112 | CFB 14.82/0.06 | Zn 7.84/0.12 | UV + HMPP 0.3/1.83 | DMAC 50 | 60/133 | 1/3 | 29.1 |
| 113 | CFB 14.82/0.06 | Zn 7.84/0.12 | UV + HMPP 0.3/1.83 | DMAC 150 | 120/136 | 1/3 | 27.6 |
| 114 | CFB 14.82/0.06 | Zn 15.68/0.24 | UV + HMPP 0.3/1.83 | DMAC 50 | 120/135 | 1/2 | 30.0 |
| 115 | CFB 14.82/0.06 | Zn 7.84/0.12 | UV + HMPP 1.0/6.1 | DMAC 50 | 120/134 | 1/4 | 30.5 |
| Comparative example 4 | CFB 29.64/0.12 | Zn 15.68/0.24 | UV | DMAC 100 | 120/130 | 2/20 | 35.7 |

Note:
The above chemical name is as follows.
AIBN 2,2-azobisisobutyronitrile
HMPP 2-hydroxy-2-methyl-1-phenyl-1-propanone
HCPK 1-hydroxy-cyclohexyl-phenyl ketone
BDK benzyl α,α-dimethyl ketal
BPO benzoyl peroxide
DTBPO diphenyl-(2,4,6-trimethylbenzoyl)phosphine oxide
EAQ 2-ethylanthraquinone
MPMPO 2-methyl-1-[4-(methylthio)phenyl]-2-morpholino-propane-1-one Although the present invention has been explained in relation to its preferred embodiment, it is understood that many other possible modifications and variations can be made without departing from the spirit and scope of the invention as hereinafter claimed.

What is claimed is:

1. A method of preparing parylene AF4 (octafluoro-[2,2]-paracyclophane), which comprises the steps of:
  (A) providing a reactant, a reducing agent, and a catalyst, wherein:
    (i) the reactant is at least one selected from the group consisting of 1,4-bis(chlorodifluoromethyl)benzene, 1,4-bis(bromodifluoromethyl)benzene, and 1,4-bis(iododifluoromethyl)benzene;
    (ii) the reducing agent is at least one selected from the group consisting of zinc, nickel, lead, aluminum, copper, magnesium and tin; and
    (iii) the catalyst is at least one selected from the group consisting of an alkali earth metal salt; an alkali earth metal oxide; an alkali earth metal hydroxide; an amphoteric element salt; an amphoteric element oxide; an amphoteric element hydroxide; an amphoteric element peroxide; an amphoteric element salt containing hydrate; a non-metallic element acid; a non-metallic element oxide; a halogen, wherein the halogen is at least one selected from the group consisting of bromine and iodine; a phase transfer catalyst of quaternary ammonium salt; a phase transfer catalyst of quaternary phosphonium salt; and a phase transfer catalyst of crown ether,
  wherein:
    the alkali earth metal salt is at least one selected from the group consisting of $CaCl_2$, $CaCO_3$, $CaSO_4$, $MgCl$, $MgSO_4$, $MgCO_3$, $Ba(NO_3)_2$ and $BaCl_2$;
    the amphoteric element salt is at least one selected from the group consisting of PbCl, $Pb(NO_3)_2$, and $SnCl_2$;
    the amphoteric element salt containing hydrate is at least one selected from the group consisting of $Pb(CH3COO)_2.3H_2O$ and $Al(NO_3)_3*9H_2O$:
    the non-metallic element acid is boric acid;
    the phase transfer catalyst of quaternary ammonium salt is at least one selected from the group consisting of tetramethyl ammonium chloride (PTC-$A_1$), phenyl trimethyl ammonium chloride (PTC-A$_2$), and benzyl triethyl ammonium chloride (PTC-A$_3$):
the phase transfer catalyst of quaternary phosphonium salt is at least one selected from the group consisting of tetraphenyl phosphonium bromide (PTC-B1) and methyl triphenyl phosphonium bromide (PTC-B2); and
the phase transfer catalyst of crown ether is at least one selected from the group consisting of 18-crown-6-ether, 12-crown-4-ether, and 15-crown-5-ether; and
(B) forming a mixture by adding the reactant, the reducing agent, and the catalyst into an aprotic polar solvent; and
(C) heating the mixture to obtain the parylene AF4.

2. The method according to claim 1, wherein the aprotic polar solvent in step (B) is at least one selected from the group consisting of N,N-dimethylacetamide, dimethylsulfoxide, dimethylformamide, tetrahydrofurane, N-methylpyrrolidone, and acetonitrile.

3. The method according to claim 1, wherein the catalyst comprises boric acid.

4. The method according to claim 1, wherein the catalyst comprises phosphorus pentoxide.

5. The method according to claim 1, wherein the catalyst comprises a phase transfer catalyst of quaternary ammonium salt, and the phase transfer catalyst of quaternary ammonium salt is at least one selected from the group consisting of PTC-A$_1$ and PTC-A$_2$.

6. The method according to claim 1, wherein the catalyst comprises a phase transfer catalyst of quaternary phosphonium salt, and the phase transfer catalyst of quaternary phosphonium salt is PTC-B$_1$.

7. The method according to claim 1, wherein the catalyst comprises a phase transfer catalyst of crown ether, and the phase transfer catalyst of crown ether is 18-crown-6-ether.

8. The method according to claim 1, wherein in the mixture formed in step (B), the weight ratio of the reducing agent to the reactant is 1:1-5.

9. The method according to claim 1, wherein in the mixture formed in step (B), the weight ratio of the reactant to the solvent is 1:1-30.

10. The method according to claim 1, wherein in the mixture formed in step (B), the weight ratio of the catalyst to the reactant is 1:10-500.

11. The method according to claim 1, wherein in step (C) the mixture is heated at a temperature of from 50-250° C.

12. The method according to claim 1, wherein the catalyst comprises at least one alkali earth metal oxide, and the alkali earth metal oxide is at least one selected from the group consisting of MgO and CaO.

13. The method according to claim 1, wherein the catalyst comprises an alkali earth metal hydroxide, and the alkali earth metal hydroxide is Ca(OH)$_2$.

14. The method according to claim 1, wherein the catalyst comprises at least one amphoteric element oxide, and the amphoteric element oxide is at least one selected from the group consisting of PbO and Pb$_3$O$_4$.

15. The method according to claim 1, wherein the catalyst comprises an amphoteric element hydroxide, and the amphoteric element hydroxide is Al(OH)$_3$.

16. The method according to claim 1, wherein the catalyst comprises a non-metallic element oxide, and the non-metallic element oxide is P$_2$O$_5$.

17. The method according to claim 1, wherein the catalyst comprises at least one selected from the group consisting of CaCl$_2$, PbCl$_2$, MgCl$_2$, BaCl$_2$, and SnCl$_2$.

* * * * *